United States Patent
Klingelhoefer et al.

(10) Patent No.: US 11,591,545 B2
(45) Date of Patent: Feb. 28, 2023

(54) METHOD OF PRODUCING BIODIESEL

(71) Applicant: BASF SE, Ludwigshafen am Rhein (DE)

(72) Inventors: Paul Klingelhoefer, Ludwigshafen (DE); Michael Koch, Ludwigshafen (DE); Michael Schier, Ludwigshafen (DE); Juergen Schneider, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 17/284,020

(22) PCT Filed: Oct. 7, 2019

(86) PCT No.: PCT/EP2019/077064
§ 371 (c)(1),
(2) Date: Apr. 9, 2021

(87) PCT Pub. No.: WO2020/074435
PCT Pub. Date: Apr. 16, 2020

(65) Prior Publication Data
US 2021/0380900 A1    Dec. 9, 2021

(30) Foreign Application Priority Data
Oct. 10, 2018    (EP) .................................... 18199610

(51) Int. Cl.
*C11C 3/02*    (2006.01)
*C07C 67/08*    (2006.01)
*B01J 31/02*    (2006.01)
*C07C 67/03*    (2006.01)

(52) U.S. Cl.
CPC ............ *C11C 3/02* (2013.01); *B01J 31/0225* (2013.01); *C07C 67/03* (2013.01); *C07C 67/08* (2013.01)

(58) Field of Classification Search
CPC ........... C11C 3/02; C07C 67/02; C07C 67/03; C07C 67/08; B01J 31/0225
See application file for complete search history.

(56) References Cited

U.S. PATENT DOCUMENTS

| | | | | |
|---|---|---|---|---|
| 4,608,202 A | * | 8/1986 | Lepper | ...................... C11C 3/04 554/167 |
| 2004/0209953 A1 | | 10/2004 | Wai | |
| 2016/0289578 A1 | * | 10/2016 | Slade | ........................ C11C 3/02 |

FOREIGN PATENT DOCUMENTS

| | | | |
|---|---|---|---|
| EP | 1892232 A1 * | 2/2008 | ............. C07C 67/03 |
| FR | 2929621 A1 | 10/2009 | |
| WO | 2008007231 A1 | 1/2008 | |

OTHER PUBLICATIONS

International Search Report issued in PCT/EP2019/077064, dated Dec. 19, 2019, pp. 1-2.
International Preliminary Report on Patentability issued in PCT/EP2019/077064, dated Mar. 3, 2021, pp. 1-8.

* cited by examiner

*Primary Examiner* — Yate' K Cutliff
(74) *Attorney, Agent, or Firm* — ArentFox Schiff LLP

(57) ABSTRACT

The present invention relates to a method of producing fatty acid alkyl ester from an organic oil source containing at least one free fatty acid, wherein the oil source has an acid number of at least 30 mg KOH/g oil source and wherein the method comprises the steps of a) reacting the oil source with glycerol at a temperature, which does not exceed 180° C. during the reaction, in the presence of a catalyst comprising at least one alkyl or aryl sulfonic acid or an homoanhydride thereof; and b) transesterification of the reaction product from step a) with an alkanol; and c) isolating the fatty acid alkyl ester from the reaction product of step b).

20 Claims, No Drawings

METHOD OF PRODUCING BIODIESEL

CROSS-REFERENCE TO RELATED APPLICATIONS

This application is a National Stage Entry of PCT/EP2019/077064, filed Oct. 7, 2019, which claims priority to EP application No. 18199610.9, filed Oct. 10, 2018, the disclosures of each of which are hereby incorporated by reference in their entireties.

The present invention relates to a method of producing fatty acid alkyl ester from an organic oil source containing at least one free fatty acid, wherein the oil source has an acid number of at least 30 mg KOH/g oil source and wherein the method comprises the steps of a) reacting the oil source with glycerol at a temperature, which does not exceed 180° C. during the reaction, in the presence of a catalyst comprising at least one alkyl or aryl sulfonic acid or an homoanhydride thereof; and b) transesterification of the reaction product from step a) with an alkanol; and c) isolating the fatty acid alkyl ester from the reaction product of step b).

Owing to their suitability as a diesel fuel ("biodiesel"), fatty acid esters have gained particular significance in recent times for reasons of environmental protection, and of the replacement of fossil energy sources (mineral oil) by renewable energy sources.

The preparation of the fatty acid esters has been known for some time. Especially biodiesel is now obtained on the industrial scale by means of a catalytic transesterification of vegetable oil. Usually dewatered, deacidified and degummed oil is reacted with a molar alcohol excess (usually methanol) of 6:1 using 1% by weight of catalyst based on the amount of the oil used (usually KOH or $NaOCH_3$) below the boiling temperature of the alcohol. The fatty acids present in the fat molecules of the oil are catalytically eliminated and react with the alcohol present to give the fatty acid ester. Fats and oils are generally triglycerides, so that that a fat molecule comprises three fatty acids bonded to one glycerol molecule. A complete transesterification reaction, as performed in the production of biodiesel, thus generates three "molecules of biodiesel" and one molecule of glycerol per molecule of fat or oil. Intermediates of this reaction are mono- and diglycerides. Mono- and diglycerides consist of a glycerol base skeleton, also referred to hereinafter as glycerol backbone, to which one fatty acid (monoglyceride) or two fatty acids (diglyceride) are bonded. Since both polar hydroxyl groups and apolar hydrocarbon chains are present in mono- and diglycerides, they have amphiphilic properties and, in organic solvents, almost always change the polarity of this solvent.

After the reaction, the glycerol formed, which is insoluble in the fatty acid alkyl ester (FAAE) is removed from the biodiesel by means of a phase separation and, after a chemical and distillation purification, utilized as an industrial or pharmaceutical raw material.

The excess alcohol present in the fatty acid alkyl esters (FAAE) is removed by means of distillation and recycled into the process. After removal and recycling of the excess alcohol, the remaining alkaline catalysts (e.g. KOH) are neutralized by adding a dilute organic or inorganic acid and, on completion of phase separation, the fatty acid ester phase is drawn off. Such a process is disclosed, for example, in EP 0 658 183 A1. Organic or inorganic acids mentioned include phosphoric acid, sulfuric acid, hydrochloric acid, nitric acid, boric acid, formic acid, acetic acid, lactic acid, gluconic acid, oxalic acid, succinic acid, maleic acid, tartaric acid, malic acid and citric acid, and also organic sulfonic acids and sulfuric monoesters. Sulfuric acid is currently used with preference in the neutralization of the alkaline catalysts. WO 2010/055158 A1 describes the use of methanesulfonic acid for neutralization of basic (alkaline) catalyst in the transesterification step.

However, some oils and especially in case of waste oils as source of glycerides to be converted into biodiesel contain high amounts of free fatty acids (FFA) not bound to glycerol. Also other biological oil sources with high amounts of FFA are available, which can in principle be used to produce biodiesel but not by classical refining steps. However these biological oil sources are often inexpensive and cannot be used in food industry. The presence of the free fatty acids in the biological oil source can result in pour catalyzed transesterification efficacy with low molecular alcohols, like methanol, due to soap formation and in pour phase separation efficacy. Thus it is suggested reacting FFA containing oil sources with glycerol in order to minimize free fatty acid content followed by the usual transesterification.

US 2016/0230106 A1 describes the acidification of waste oil compositions by acid washing to produce a composition comprising free fatty acids derived from the waste oil composition and converting the same into glycerides followed by transesterification to yield a biodiesel composition. However a catalyst free reaction results in uncomplete reaction or harsh reaction conditions which cause side product formation. US 2005/075509 A1 also describes a process starting with the reaction of glycerides and free fatty acids with glycerol without catalyst and subsequent transesterification.

U.S. Pat. No. 6,822,105 B1 describes a process starting with the reaction of glycerides and free fatty acids with glycerol in the presence of a catalyst selected from organotin compounds, organo titanium compounds, alkali acetates, earthalkali acetates, lewis acids, alkali carbonates, earthalkali carbonates, and combinations thereof and subsequent transesterification. However the mentioned metal containing catalysts are expensive and result in additional process steps to remove undesired metal salts.

CN 104450209 A describes a method for reducing the acid value of crude rice bran oil through solid super acid catalysis. The method comprises the following steps: adding glycerol and a solid super acid catalyst into crude rice bran oil with a high acid value, heating, stirring, vacuuming to remove water generated from reaction, after the reaction is completed, filtering and recycling the catalyst, thereby obtaining rice bran oil with a low acid value. However the use of solid super acid catalysts is expensive.

WO 2008/007231 A1 and WO 2009/068940 A1 describe an esterification process of fatty acid substances with glycerol in the presence of various catalysts and a reaction end temperature of about 230° C. However the high temperature is cost-intensive and causes side products.

CN 101880602 A describes the esterification of high acid value oil using high acid value oil as raw material, adding a solid catalyst, adding crude glycerol to the high acid value oil by a dropping method and refluxing the esterification reaction under vacuum condition. However the use of solid catalysts results in more complicated reaction equipment due to the heterogeneous phase system.

WO 2010/141917 A2 describes the production of biodiesel oil starting from a raw material comprising a fatty acid and oil, which is contacted with glycerol and a Lewis acid catalyst in form of tetrabutyl titanate (TBT) at temperatures between 150 and 200° C. However such catalysts are expensive.

CN 103173293 A relates to a method for preparing biodiesel by utilizing high-acid value oil. The method comprises the steps of esterifying the raw materials of the high-acid value oil, enabling glycerol and the raw materials of the high-acid value oil to esterify with each other under the catalyzing action of an ionic liquid, and thus obtaining a mixture of a low-acid value esterification product-monoglyceride, diglyceride or triglyceride. Also CN 104194946 A describes the use of an ionic liquid catalyst. However the handling of ionic liquids results in high demand regarding the reaction equipment.

KR 10-2017-0043906 A describes a method for converting High Acid Value Fatty Acid to Bio Fuel Oil or Biodiesel, wherein a fatty acid is converted into a fat oil by adding glycerol in the presence of sulfuric acid or methanesulfonic acid at 200-250° C.

EP 1 892 232 A1 describes the production of esters of fatty acids and lower alcohols. In example 6 a FFA rich stream is esterified with glycerol in the presence of para toluene sulfonic acid.

FR 2 929 621 A1 describes a process for the esterification of FFA in a fatty substance with an alcohol, like methanol, ethanol, glycerol, preferably methanol, in the presence of methane sulfonic acid at a temperature of 45 to 70° C.

Thus it is an object of the present invention to provide a process for biodiesel production which avoids or reduce the disadvantageous drawbacks caused by related art processes.

This object is achieved by a method of producing fatty acid alkyl ester from an organic oil source containing at least one free fatty acid, wherein the oil source has an acid number of at least 30 mg KOH/g oil source and wherein the method comprises the steps of a) reacting the oil source with glycerol at a temperature, which does not exceed 180° C. during the reaction, in the presence of a catalyst comprising at least one alkyl or aryl sulfonic acid or an homoanhydride thereof; and b) transesterification of the reaction product from step a) with an alkanol; and c) isolating the fatty acid alkyl ester from the reaction product of step b).

It was surprisingly found that the use of at least one alkyl or aryl sulfonic acid or an homoanhydride thereof, especially methanesulfonic acid, as catalyst in step a) in combination with a reaction temperature, which does not exceed 180° C. results in a high efficient biodiesel production due to a low free acid containing intermediate product from step a), preferably with an acid number of or below 20 mg KOH/g oil source, preferably of or below 10 mg KOH/g oil source, more preferably of or below 2 mg KOH/g oil source, combined with low tendency of by-product formation and cost-effective catalyst amount and reaction equipment.

The process can be carried out throughout a broad range of oil qualities and different organic oil sources having a content of free fatty acid of at least 15% by weight, which relates to an acid number of about 30 mg KOH/g oil source. Furthermore the esterification in step a) can be carried out using standard esterification equipment with low costs, especially when using a downflow evaporator. It is further advantageous that a phase separation is not required between steps a) and b), especially in case step b) is an alkaline transesterification. Also after the transesterification step a phase separation can be easily carried as there is sufficient density difference between the biodiesel and the glycerol/methanol phase.

One or more pretreatment steps can precede step a) of the method according to the present invention in order to quality the oil source. Such steps are, e.g., filtration and degumming steps.

Surprisingly low catalyst concentration is required forming an economic process and low corrosion levels are achieved, especially compared to the commonly used sulfuric acid, which results in low procurement and maintenance costs.

The alkyl or aryl sulfonic acid or an homoanhydride thereof as catalyst is advantageous compared to sulfuric acid as common acidic catalyst since no or decreased tendency of decomposition of glycerol can be observed due to oxidation, water elimination and sulfatation. Furthermore a good salt solubility in glycerol/methanol phase is given and lower acid number can be obtained. In addition methanesulfonic acid is quite more preferred compared to p-toluenesulfonic acid as the use of methanesulfonic acid results in a lower amount of sulfur in the biodiesel phase and processing is easier as methanesulfonic acid is liquid (commercially available as 70% concentration in water) at room temperature (melting point $-54°$ C.), which is also advantageous compared to solid catalysts.

The starting material in the process of producing FAAE's is an organic oil source.

Organic oil is produced in contrast to mineral oil by plants, animals and other organisms through natural metabolic processes and is glyceride based. The term "organic oil source" is to be understood to include organic oil, like vegetable oil and animal oil, especially vegetable oil, but also any other mixture, by-product or fraction of organic oil that contains at least one FFA and is suitable to produce biodiesel according to the method of producing FAAE according to the present invention. The term "organic oil source" also includes fats, which are solid at room temperature, but liquid at the reaction temperature in step a) of the method of producing FAAE according to the present invention.

Organic oil sources typically contain different types of free fatty acids in different amounts as well as fatty acid bound as tri-, di- and monoglycerides. Only very low amounts—if any—of other organic acids can be included so that in industry the acid number measurement is used to quantify the amount of all free fatty acids contained in the organic oil source. Measurement can be carried out in analogy of the standard method DIN EN 14104 (2003-10).

The method of the present invention is suitable for organic oil sources with an acid number of at least 30 mg KOH/g oil source. Preferably, the oil source has an acid number of at least 40 mg KOH/g oil source, more preferably at least 60 mg KOH/g oil source, even more preferably at least 80 mg KOH/g oil source, even more preferably at least 100 mg KOH/g oil source, even more preferably at least 120 mg KOH/g oil source, even more preferably at least 140 mg KOH/g oil source, even more preferably at least 150 mg KOH/g oil source.

Organic oil sources include vegetable and animal oils and fats. Vegetable oils are generally obtained by extraction from seeds, by means of solvent or pressure, while animal fats are obtained by hot extraction in autoclaves or by means of solvent. Normally these fatty substances contain free fatty acids, sterols, phospholipids, water, odorous substances and other impurities. Refining of the fatty substances involves complete removal of nearly all the impurities including the free fatty acids so that they can be used in the production of biodiesel, in food and in industry in general.

Refined vegetable and animal oils and fats typically show very low FFA content. However during use of these refined oils and fats the FFA content can increase.

Used oils typically show high amounts of free fatty acid and thus also have high acid numbers. Thus, in a preferred embodiment of the present invention the organic oil source is from used vegetable and/or animal oil and/or fat, like used cooking oil. Used oil is also called waste oil, so that waste oil, especially waste vegetable oil, is preferred.

Other organic oil sources include by-products of the chemical and physical refining of vegetable and/or animal oil and/or fat, by-products of the refining of glycerine from biodiesel, fatty acids from distillation and non-distillation, hydrolytically cleaved fatty substances, trap grease and distilled and non-distilled fatty acids resulting from the cleaving of soaps.

Also mixtures of the above organic oil sources are encompassed.

Preferably, the organic oil source is from used vegetable oil or by-products of the chemical and physical refining of vegetable oil. The vegetable oil is preferably an oil or oil mixture selected from the group of oils consisting of coconut oil, corn oil, cottonseed oil, olive oil, palm oil, peanut oil, rapeseed oil, safflower oil, sesame oil, soybean oil and sunflower oil, preferably the vegetable oil comprises rapeseed oil, even more preferably the vegetable oil is palm oil.

More preferably, the organic oil source is palm fatty acid distillate (PFAD) or palm sludge oil (PSO). PAFD is a lower-value by-product generated during the refining of palm oil in the fatty acid stripping and deodorization stages. PFAD is generally sold as a source of industrial fatty acids for non-food applications.

Even more preferably, the organic oil source is palm sludge oil (PSO). It is an un-distilled residue of palm oil production with inferior quality compared to PFAD.

The organic oil source may be purified before used in step a) of the method for producing FAAE. An optional purification step is the removal of metal ions, e.g. be using complexation agents (chelate formation). Also washing steps may be used before step a). Suitable washing steps include water and acidic washing. This may be used to remove inorganic acids or the like.

Preferably, the at least one free fatty acid is a fatty acid or a mixture of fatty acids selected from the group of fatty acids consisting of caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linolelaidic acid, alpha-linoleic acid, arachidonic acid, eicosapentaenoic acid, erucic acid and docosahexaenoic acid, preferably the at least one free fatty acid comprises or consists of oleic oil and/or palmitic oil. Accordingly, the term "at least one fatty acid" is to be understood in that the at least one fatty acid is specific fatty acid or a mixture of two, three or more fatty acids (mixture of fatty acids).

These fatty acids are converted into alkyl esters to yield FAAE's as biodiesel. However, the most preferred alkyl ester is the methyl ester so that fatty acid methyl esters (FAME's) are preferred. Preferably, the biodiesel obtained by the method of producing FAME according to the present invention fulfills the requirements of DIN EN 14214 (2014-06).

In step a) of the method of producing FAAE according to the present invention the organic oil source is reacted with glycerol at a temperature, which does not exceed 180° C. during the reaction. The apparatus to be used is in principle known to the practitioner in the art. A preferred reaction equipment for carrying out step a) is a downflow evaporator.

Preferably, during the reaction in step a) the temperature does not exceed 170° C., more preferably does not exceed 160° C., even more preferably the temperature does not exceed 150° C. Preferably, in step a) the temperature is at least 110° C., more preferably at least 120° C., even more preferably at least 130° C. Accordingly preferred temperature ranges are from 110° C. to 180° C., more preferably the temperature is from 110° C. to 170° C., even more preferably from 120° C. to 160° C. and even more preferably from 130° C. to 150° C. A preferred temperature is 140° C.

Step a) of the method of producing FAAE of the present invention, is carried out in the presence of a catalyst comprising at least one alkyl or aryl sulfonic acid or an homoanhydride thereof. Accordingly, the catalyst can comprise and can consist of one alkyl sulfonic acid, one aryl sulfonic acid, two or more, like three, four or five alkyl sulfonic acids, two or more, like three, four or five aromatic sulfonic acids or one or more alkyl sulfonic acids and one or more aryl sulfonic acids. The same applies to their homoanhydrides. However preferably, the catalyst comprises or is an alkyl or an aryl sulfonic acid.

The term "alkyl sulfonic acid" preferably refers to an acid of formula $R^a$—$SO_3H$, wherein $R^a$ is an alkyl group having 1 to 4 carbon atoms, which are straight-chained or branched, i.e. methyl, ethyl, i-propyl, n-butyl, sec-butyl, i-butyl, tert.-butyl. Preference is given to methyl, i.e. methanesulfonic acid.

The term "aryl sulfonic acid" preferably refers to an acid of formula $R^b$—$SO_3H$, wherein $R^b$ is an aryl group having 6 to 16 carbon atoms, which comprises at least one benzene ring that can be substituted by an alkyl group as defined for the alkyl sulfonic acid. An example is p-toluenesulfonic acid.

Preferably, the alkyl or aryl sulfonic acid or homoanhydride thereof is methanesulfonic acid, methanesulfonic acid anhydride, para-toluenesulfonic acid or para-toluenesulfonic acid anhydride, more preferably methanesulfonic acid or methanesulfonic acid anhydride and even more preferably methanesulfonic acid.

Preferably, the alkyl or aryl sulfonic acid is methanesulfonic acid or para-toluenesulfonic acid, more preferably methanesulfonic acid. The alkyl or aryl sulfonic acid can be introduced into the reaction mixture in liquid or solid form, preferably in liquid from. A liquid form includes the acid as such in the liquid state or solved in a liquid, like water. Especially in case of methanesulfonic acid the liquid state is preferred, which is advantageous compare to heterogeneous catalysts. Preferably, the reaction in step a) has a reaction time of more than one hour and less than 12 hours. Preferably, the reaction time starts when the desired (minimum) reaction temperature has been reached. Preferably, the reaction time is from 2 hours to 10 hours, even more preferably, from 3 hours to 9 hours, even more preferably from 4 to 8 hours.

Since in step a) also water is a reaction product suitable measures should be taken to reduce the water content formed by the reaction. Preferably, the reaction in step a) is carried out under reduced pressure (relative to atmospheric pressure). More preferably, the pressure is below 1000 hPa, more preferably 900 hPa or lower, even more preferably 800 hPa or lower, even more preferably, 700 hPa or lower, even more preferably, 600 hPa or lower, even more preferably 500 hPa or lower, even more preferably 400 hPa or lower, even more preferably 300 hPa or lower, even more preferably 200 hPa or lower, even more preferably 100 hPa or lower.

Preferably, in step a) the initial molar ratio of glycerol to free fatty acid calculated on the basis of the acid number of the oil source is from 1:2 to 1.2:1, more preferably from 1:2 to 1:1, even more preferably from 3:5 to 9:10, even more preferably from 2:3 to 9:10.

Preferably, in step a) the amount of the alkyl or aryl sulfonic acid is from 0.2 to 0.6 weight-%, even more preferably from 0.2 to 0.6 weight-%, even more preferably from 0.25 to 0.55 weight %, even more preferably from 0.3 to 0.5 weight-%, based on the total amount of the oil.

In step b) a transesterification is carried out with an alkanol, preferably methanol to yield FAME. Transesterifications of fatty acid glycerides to yield lower alkyl glycerides are well known in the art. Typically the transesterification can be carried out in the presence or absence of a catalyst. Preferably a catalyst is used. The reaction can be carried out by base or acid catalysis. Basic (alkaline) catalysis is preferred. Here a preferred catalyst is potassium hydroxide. Methanesulfonic acid can be used for a neutralization of the alkaline catalyst as described in WO 2010/055158 A1. Excess of methanol can be separated and recycled for step b) of the method of producing FAAE according to the present invention.

The transesterification in step b) can generally be carried out in one stage or in two or more stages, i.e. the fatty acid glyceride is either transesterified with the entire amount of alkanol and catalyst, or only a portion of the amount of alkanol and catalyst required is used for transesterification in a first stage and, on completion of settling and removal of a glycerol phase, the remaining amount(s) of alkanol and catalyst are used for transesterification in the same way in a second stage or in further stages, the two- and multistage bringing the advantage of a further decrease in the alcohol excess and additionally increased yields of fatty acid ester.

When the transesterification is effected, in one embodiment of the invention, by the two-stage method, preferably 60% to 90% of the total amount of alkanol and catalyst required is used in the first stage, and 10% to 40% of the total amount of short-chain alcohol and catalyst in the second stage.

The transesterification in the method according to the invention is typically effected at about 60° C. and atmospheric pressure, and can in principle be performed in any desired open or closed vessel of any size, which is advantageously equipped with a discharge device at the bottom. The process according to the invention can equally be performed using stirrer devices or mechanical intensive mixers. The corresponding apparatuses and embodiments are known to those skilled in the art in the field of apparatus technology.

In the presence of suitable metering apparatus, of a suitable reactor and of an appropriate monitoring system, the method for producing FAAE according to the invention can also be performed continuously.

Useful basic catalysts for the transesterification in step b) are alkali metal or alkaline earth metal compounds in the form of the oxides, hydroxides, hydrides, carbonates, acetates or alkoxides of the alkanol, preferably sodium hydroxide, potassium hydroxide, or sodium and potassium alkoxides of the short-chain monohydric alcohols having 1 to 5 carbon atoms. The basic catalysts are more preferably selected from KOH, NaOH, sodium methoxide and potassium methoxide. Especially preferred are potassium methoxide and sodium methoxide.

In a general embodiment of the invention, the basic catalyst is used in the transesterification of the fatty acid glycerides in an amount of 0.1 to 5% by weight, preferably in an amount of 0.5 to 1.5% by weight, based on the mass of the fatty acid glyceride used. The lower monohydric alcohol is added in an excess of 0.1 mol to 2.0 mol, based on 1 mol each of fatty acid bound to glycerol. If appropriate, water is used in an amount of 0.5 to 20% by weight based on the reaction mixture in the transesterification of the fatty acid glycerides.

In a general embodiment of the invention, the basic catalyst is added to the fatty acid glyceride in the form of an aqueous or alcoholic solution.

Preferably, between step a) and step b) no phase separation is carried out.

Preferably, after step a) and before step b) the at least one alkyl or aryl sulfonic acid, and optionally residual FFA, is neutralized, preferably with an alkali metal carbonate, like sodium or potassium carbonate.

In step c) the reaction product (biodiesel) is isolated. Any known isolation method can be used. Preferably, in step c) the isolation includes a distillation step. This distillation is useful to convert crude biodiesel into biodiesel of higher purity. Before distillation phase separation may be used to recover glycerol, which in turn may be further purified, e.g. also by distillation.

In a preferred embodiment step a) is carried out in the presence of at least one anionic surfactant S.

Anionic surfactant in general means a surfactant with a negatively charged ionic group. Anionic surfactants S, in the context of this invention contain a hydrophobic group and at least one water-solubilizing anionic group selected from sulfates, sulfonates, phosphonates and phosphates to form a water-soluble compound. It is to be understood that such anionic surfactants may be at least partly protonated.

Anionic surfactants S may be compounds of general formula (VIII), which might be called (fatty) alcohol/alkyl (ethoxy/ether) sulfates [(F)A(E)S] when A- is SO3 or (fatty) alcohol/alkyl(ethoxy/ether) carboxylat [(F)A(E)C] when A- is —RCOO—:

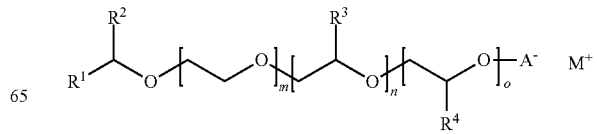

(VIIIa)

-continued

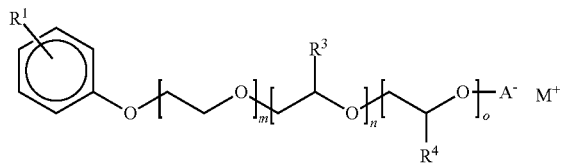
(VIIIb)

The variables in general formula (VIII) are defined as follows:

$R^1$ is selected from $C_1$-$C_{23}$-alkyl and $C_2$-$C_{23}$-alkenyl, wherein alkyl and/or alkenyl are linear or branched. Examples are n-$C_7H_{15}$, n-$C_9H_{19}$, n-4-$C_9H_{19}$, n-$C_{11}H_{23}$, n-$C_{13}H_{27}$, n-$C_{15}H_{31}$, n-$C_{17}H_{35}$, i-$C_9H_{19}$, i-$C_{12}H_{25}$.

$R^2$ is selected from H, $C_1$-$C_{20}$-alkyl and $C_2$-$C_{20}$-alkenyl, wherein alkyl and/or alkenyl are linear or branched.

$R^3$ and $R^4$ are each independently selected from $C_1$-$C_{16}$-alkyl, wherein alkyl is linear or branched. Examples are methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, nheptyl, n-octyl, 2-ethylhexyl, n-nonyl, n-decyl, isodecyl.

A is selected from —$SO_3$— and —$RSO_3$—, $PO_3^{2-}$ and $RPO_3^{2-}$, wherein R is selected from $C_1$-$C_{18}$-alkylene, wherein alkylene is linear or branched.

M is selected from H and salt forming cations. Salt forming cations may be monovalent or multivalent; hence M+ equals 1/v Mv+. Examples include but are not limited to sodium, potassium, magnesium, calcium, ammonium, and the ammonium salt of mono-, di, and triethanolamine (TEA).

The integers of the general formulae (VIIIa) and (VIIIb) are defined as follows:

m is in the range from zero to 200, preferably 1-80, more preferably 3-20; n and o, each independently in the range from zero to 100; n preferably is in the range from 1 to 10, more preferably 1 to 6; o preferably is in the range from 1 to 50, more preferably 4 to 25. The sum of m, n and o is at least one, preferably the sum of m, n and o is in the range from 5 to 100, more preferably in the range of from 9 to 50.

Anionic surfactants of the general formula (VIII) may be of any structure, block copolymers or random copolymers.

Further non-limiting examples of suitable anionic surfactants include salts (M+) of sulfates or sulfonates derived from natural fatty acids such as tallow, coconut oil, palm kernel oil, laurel oil, olive oil, or canola oil. Such anionic surfactants comprise sulfates or sulfonates of lauric acid and/or myristic acid and/or palmitic acid and/or stearic acid and/or oleic acid and/or linoleic acid in different amounts, depending on the natural fatty acids from which the soaps are derived.

Further suitable anionic surfactants include salts (M+) of $C_{12}$-$C_{18}$ alkylsulfonic acids, $C_{12}$-$C_{18}$ sulfonated fatty acid alkyl esters (such as $C_{12}$-$C_{18}$ sulfo fatty acid methyl esters), $C_{10}$-$C_{18}$-alkylarylsulfonic acids (such as n-$C_{10}$-$C_{18}$-alkylbenzene sulfonic acids) and $C_{10}$-$C_{18}$ alkyl alkoxy carboxylates.

M+ in all cases is selected from salt forming cations. Salt forming cations may be monovalent or multivalent; hence M+ equals 1/v Mv+. Examples include but are not limited to sodium, potassium, magnesium, calcium, ammonium, and the ammonium salt of mono-, di, and triethanolamine (TEA).

Non-limiting examples of further suitable anionic surfactants include branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, secondary alkanesulfonates (SAS), paraffin sulfonates (PS), sulfonated fatty acid glycerol esters, alkyl- or alkenylsuccinic acid, fatty acid derivatives of amino acids, diesters and monoesters of sulfo-succinic acid.

Anionic surfactants may be compounds of general formula (IX), which might be called N-acyl amino acid surfactants:

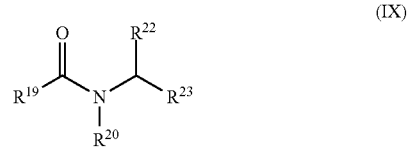
(IX)

The variables in general formula (IX) are defined as follows:

$R^{19}$ is selected from $C_6$-$C_{22}$-alkyl, wherein alkyl is linear or branched.

$R^{20}$ is selected from H and $C_1$-$C_4$-alkyl.

$R^{22}$ is selected from methyl, —$(CH_2)_3$NHC(NH)$NH_2$, —$CH_2C(O)NH_2$, —$CH_2C(O)OH$, —$(CH_2)_2C(O)NH_2$, —$(CH_2)_2C(O)OH$, (imidazole-4-yl)-methyl, —$CH(CH_3)$ $C_2H_5$, —$CH_2CH(CH_3)_2$, —$(CH_2)_4NH_2$, benzyl, hydroxymethyl, —$CH(OH)CH_3$, (indole-3-yl)-methyl, (4-hydroxyphenyl)methyl, and isopropyl.

$R^{23}$ is selected from —COOX and —$CH_2SO_3X$, wherein X is selected from Li+, Na+ and K+.

Non-limiting examples of further suitable N-acyl amino acid surfactants are the mono- and dicarboxylate salts (e.g., sodium, potassium, ammonium and TEA) of N-acylated glutamic acid, for example, sodium cocoyl glutamate, sodium lauroyl glutamate, sodium myristoyl glutamate, sodium palmitoyl glutamate, sodium stearoyl glutamate, disodium cocoyl glutamate, disodium stearoyl glutamate, potassium cocoyl glutamate, potassium lauroyl glutamate, and potassium myristoyl glutamate; the carboxylate salts (e.g., sodium, potassium, ammonium and TEA) of N-acylated alanine, for example, sodium cocoyl alaninate, and TEA lauroyl alaninate; the carboxylate salts (e.g., sodium, potassium, ammonium and TEA) of N-acylated glycine, for example, sodium cocoyl glycinate, and potassium cocoyl glycinate; the carboxylate salts (e.g., sodium, potassium, ammonium and TEA) of N-acylated sarcosine, for example, sodium lauroyl sarcosinate, sodium cocoyl sarcosinate, sodium myristoyl sarcosinate, sodium oleoyl sarcosinate, and ammonium lauroyl sarcosinate.

A preferred anionic surfactant S is a $C_{10}$-$C_{18}$-alkylarylsulfonic acid, especially an n-$C_{10}$-$C_{18}$-alkylbenzene sulfonic acid.

Mixtures of two or more different anionic surfactants S may also be present according to the present invention.

Amounts of anionic surfactants may vary depending on the nature of the biological oil source.

Exemplary amounts are in the range of from 0.01 weight-% to 10 weight-%, preferably 0.05 weight-% to 10 weight-%, preferably from 0.1 to 5 weight-%, more preferably from 0.1 to 3 weight-%, more preferably from 0.5 weight-% to 1.5 weight-%, based on the total weight of the biological oil source.

EXAMPLES

Example 1: Standard Conditions Reaction Step a) According to the Method of the Invention Model biological oil source prepared from oleic acid/refined rape seed oil: 80/20 (free fatty acid content (FFA) of the oil phase: 80 wt %, Acid number (calculated) 159 mg KOH/g biological oil source="oil phase")
- temperature: 140° C.
- catalyst: methanesulfonic acid (MSA)
- methanesulfonic acid: 0.5 wt % related to the oil phase
- glycerol/oleic acid: 0.84 molar ratio
- pressure: 10 kPa 188.8 g oleic acid (=0.67 mol), 47.2 g rape seed oil (refined, acid number 0.19 mgKOH/g) (=236 g oil phase) and 59 g glycerol 87% active (=0.56 mol) were mixed in a reaction vessel and heated up to 140° C. under vacuum (10 kPa) and stirring. 1.69 g methanesulfonic acid (MSA) 70% active (=1.183 g MSA=12.3 mmol=0.5 wt % related to the oil phase) were added to the reaction mixtures. The reaction time starts at 140° C. and temperature and vacuum is kept constant at 10 kPa.

The esterification of oleic acid with glycerol was controlled by taking out samples (ca. 4 g). The sample is washed with ca. 4 g glycerol to eliminate MSA from the mixture. Glycerol and oil phase are separated. From the oil phase the acid number is measured according to DIN EN 14104.

The 0 h value is determined before the addition of MSA or in later procedure the corresponding other acids.

Example 2

The time dependency of acid number was controlled as summarized in Table 1.

TABLE 1

Time dependency of Acid number in mgKOH/g

| | 0 h | 0.5 h | 1.0 h | 2.0 h | 4.0 h | 6.0 h | 8.0 h |
|---|---|---|---|---|---|---|---|
| Example 1 | 153 | 92 | 13.2 | 3.1 | 2.1 | 1.9 | 1.7 |

Table 1 shows that from a reaction time of 4.0 hours an onwards the acid number is in the range of about 2 or below.

The reproducibility was controlled by repeating the 4 h-result for 4 times:

| 140° C. | Acid number (mgKOH/g) 4 h |
|---|---|
| Example 1 | 2.1 |
| Repeat 1 | 1.7 |
| Repeat 2 | 2.1 |
| Repeat 3 | 2.3 |
| Repeat 4 | 1.9 |

Example 2: Variation of Acid

According to the procedure of Example 1 different acids and quantities were used and summarized in Table 2.

TABLE 2

| Acid | Acid (g) | acid (g, calculated 100% active) | wt % related to the oil phase | mmol acid | Acid number (mgKOH/g) 4 h |
|---|---|---|---|---|---|
| Without | 0 | 0 | 0 | 0 | 104.7 |
| MSA (70%) (Example 1) | 1.69 | 1.18 | 0.5 | 12.3 | 2.1 |
| para-TSA[+)] | 2.36 | 2.36 | 1.0 | 13.7 | 2.60 |
| $H_2SO_4$ (conc.)** | 1.75 | 1.68 | 0.71 | 17.1 | 5.9 |
| $H_2SO_4$ (conc.)** | 1.25 | 1.2 | 0.51 | 12.2 | 5.1 |
| $H_2SO_4$ (conc.)* | 0.93 | 0.89 | 0.38 | 9.1 | 7.4 |
| $H_2SO_4$ (conc.) | 0.47 | 0.45 | 0.19 | 4.6 | 11.4 |
| 2-Ethylhexyl titanate | 1.05 | 1.0 | 0.43 | 1.8 | 82.1 |
| 2-Ethylhexyl titanate | 7.26 | 6.9 | 2.92 | 12.3 | 74.0 |
| Tin (II) chloride dihydrate | 2.8 | 2.8 | 1.19 | 12.4 | 66.0 |

[+)]para TSA = para toluenesulfonic acid
*)some precipitate formed
**)tar like by-products are formed during the reaction Table 2 shows that only MSA and p-TSA show good results, especially MSA.

Example 3: Para-Toluene Sulfonic Acid (p-TSA) at 140° C., 8 h

According to the procedure of Example 1 para-toluene sulfonic acid (13.7 mmol) was used at 140° C. for up to 8 h and in Table 3 compared with MSA.

TABLE 3

| Acid number (mgKOH/g) | 0 h | 0.5 h | 1.0 h | 2.0 h | 4.0 h | 6.0 h | 8.0 h |
|---|---|---|---|---|---|---|---|
| Example 1 (140° C.) | 153 | 92 | 13.2 | 3.1 | 2.1 | 1.9 | 1.7 |
| p-TSA (140° C.) Example 2 | 153 | 27 | 4.8 | 2.9 | 2.6 | 2.4 | 1.8 |

Reproducibility of o-TSA Results:

| 140° C. | Acid number (mgKOH/g) 4 h |
|---|---|
| Example 2 | 2.6 |
| Repeat 1 | 2.7 |
| Repeat 2 | 2.6 |

Example 4: Variation of Glycerol to Oleic Acid Ratio

According to the procedure of Example 1 different addition levels of Glycerol were used and summarized in Table 4.

TABLE 4

| Glycerol/Oleic acid (free fatty acid) molar ratio | Glycerol (g, 87%) | Glycerol (g, 100%) | mmol Glycerol | Acid number (mgKOH/g) 4 h |
|---|---|---|---|---|
| 0.30 | 21.2 | 18.4 | 200 | 24.9 |
| 0.50 | 35.4 | 30.8 | 334 | 2.8 |
| 0.6 | 42.5 | 37.0 | 401 | 2.2 |
| 0.67 | 47.2 | 41.1 | 446 | 2.1 |
| 0.84 (Example 1) | 59 | 51.3 | 560 | 2.1 |
| 1.0 | 70.8 | 61.6 | 669 | 3.7 |
| 1.2 | 84.9 | 73.9 | 802 | 3.8 |

Table 4 shows that very good results were observed with molar ratios of below 1 to about 0.5.

Example 5: Variation of Free Fatty Acid (FFA) Content in the Oil Phase (Glycerol/FFA: Molar Ratio 0.8-0.84)

According to the procedure of Example 1 different addition levels of Oleic acid, rape oil & Glycerol were tested.

TABLE 5

| FFA content in the oil phase (wt. %) | oleic acid (g) | oleic acid (mmol) | rape seed oil (g) | oil phase (g) | Glycerol (g, cal. 100%) | Glycerol (mmol) | Glycerol/FFA molar ratio | Acid number (mgKOH/g) 4 h |
|---|---|---|---|---|---|---|---|---|
| 80 (Exam. 1) | 188.8 | 670 | 47.2 | 236 | 51.3 | 560 | 0.84 | 2.1 |
| 50 | 118.0 | 418 | 118.0 | 236 | 30.8 | 334 | 0.80 | 2.2 |
| 30 | 70.8 | 251 | 165.2 | 236 | 19.3 | 210 | 0.83 | 2.0 |
| 20 | 47.2 | 167 | 188.8 | 236 | 12.9 | 140 | 0.84 | 2.2 |
| 10[+)] | 23.6 | 84 | 212.4 | 236 | 6.4 | 69 | 0.82 | 11.1 |
| 10[+)] | 23.6 | 84 | 212.4 | 236 | 12.8 | 138 | 1.64 | 2.3 |

[+)]Acid number of 20 mg KOH/g organic oil source

Example 6: Variation of Temperature

Procedure Analogous to Example 1 but Different Temperatures.

The temperature dependency was tested for different temperatures. The results are summarized in Table 6.

TABLE 6

Temperature dependency of Acid number in mg KOH/g

| Temperature (° C.) | Acid number (mgKOH/g) 4.0 h |
|---|---|
| 110 | 77.8 |
| 120 | 3.0 |

TABLE 6-continued

Temperature dependency of Acid number in mg KOH/g

| Temperature (° C.) | Acid number (mgKOH/g) 4.0 h |
|---|---|
| 140 (Example 1) | 2.1 |
| 160 | 2.3 |
| 180 | 2.5 |

Example 7: Variation of MSA (Ca. 100%) Concentration (% of Oil Phase)

According to the procedure of Example 1 different MSA concentrations were tested.

TABLE 7

MSA dependency of Acid number in mgKOH/g

| MSA wt.-% of oil phase | MSA (cal. 100%) (g) | Acid number (mgKOH/g) 4.0 h |
|---|---|---|
| 0.1 | 0.24 | 6.6 |
| 0.2 | 0.47 | 2.8 |
| 0.25 | 0.59 | 2.3 |
| 0.3 | 0.71 | 2.1 |
| 0.4 | 0.94 | 2.1 |
| 0.5 (Example 1) | 1.18 | 2.1 |
| 0.6 | 1.41 | 3.8 |

Example 8: MSA Dependency of Acid Number

The acid number of different samples with increasing content of MSA was tested and summarized in Table 8.

TABLE 8

50 wt % FFA - MSA dependency of Acid number in mgKOH/g

| MSA % of oil phase (w/w) | MSA (cal. 100%) (g) | Acid number (mgKOH/g) 4.0 h |
|---|---|---|
| 0.1 | 0.24 | 8.3 |
| 0.2 | 0.47 | 1.9 |
| 0.3 | 0.71 | 1.8 |
| 0.5 | 1.18 | 1.6 |

Example 9: Impact of the Addition of Sulfonate-Based Anionic Surfactant on the Esterification Kinetics (at 140° C.)

According to the procedure Example 1 addition of 0.5% w/w of Disponil® LDBS 55 (55% concentration in water) was tested and summarized in Table 9.

Disponil® LDBS 55:

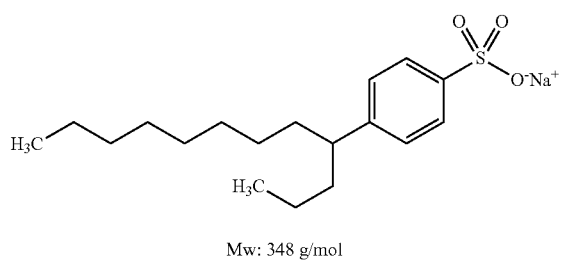

Mw: 348 g/mol

TABLE 9

Impact of the addition of sulfonate-based anionic surfactant esterification Acid number in mgKOH/g

| | 0 h | 0.5 h | 1.0 h | 2.0 h | 4.0 h |
|---|---|---|---|---|---|
| Example 1 | 153 | 92 | 13.2 | 3.1 | 2.1 |
| Example 1 + 0.5% w/w Disponil LDBS 55 | 153 | 17 | 5.6 | 2.5 | 1.7 |

Example 10: Reaction Step b) According to the Method of the Invention

Transesterification of resulting oil by reaction with glycerol without prior phase separation from the above process with Methanol:

Procedure:

1. Step Transesterification

To 250 g product from Example 1 3.76 g KOH (dissolved in 40.9 g Methanol) were added at 60° C. 1 h reaction time at 60° C. under stirring. Product was put at 60° C. in a separatory funnel. After 30 min. the phase separation was completed (oil phase at top/glycerol Methanol phase at bottom). Oil phase (229.2 g) were separated from the glycerol/methanol phase (65.4 g) and refilled into the reactor for step 2.

2. Step Transesterification 229 g oil phase were heated to 60° C. and 1.03 g KOH (dissolved in 16.0 g Methanol) were added. 1 h reaction time at 60° C. under stirring. Product was put at 60° C. in a separatory funnel. After 30 min. the phase separation was completed (oil phase at top/glycerol Methanol phase at bottom). Oil phase (223.8 g) were separated from the glycerol/methanol phase (7.4 g). Oil phase is acidified at 90° C. with 5 ml of 0.2 m MSA resulting in a pH of 1.9).

The resulting fatty acid methylester (FAME) was washed two times with water and dried by distillation of the residual water.

In both steps there is no precipitation of salt (K-mesylate). The phase separation is complete and fast also no purification step in the starting product (Example 1) was made (no phase separation in Example 1). The sulfur content in the FAME was analyzed to 17 ppm.

Transesterification with p-TSA (Example 2) was analogue to MSA (Example 1). The sulfur content in the FAME was analyzed to 32 ppm for p-TSA as catalyst.

Sulfur Content:
Oleic acid: 4 ppm,
Rape oil: <2 ppm,
Glycerol: <2 ppm.
Trace analysis of by-products:
Hydroxyacetone <50 mg/kg
Acrolein <10 mg/kg.

The invention claimed is:

1. A method of producing fatty acid alkyl ester from an organic oil source comprising at least one free fatty acid, wherein the oil source has an acid number of at least 30 mg KOH/g oil source and wherein the method comprises the steps of
    a) reacting the oil source with glycerol at a temperature, which is at least 110° C. and does not exceed 180° C. during the reaction, in the presence of a catalyst comprising at least methanesulfonic acid or the homoanhydride thereof, wherein in step a) the initial molar ratio of glycerol to free fatty acid calculated on the basis of the acid number of the oil is from 1:2 to 1.2:1
    b) transesterification of the reaction product from step a) with an alkanol; and
    c) isolating the fatty acid alkyl ester from the reaction product of step b).

2. The method of claim 1, wherein the fatty acid alkyl ester is fatty acid methyl ester.

3. The method of claim 1, wherein the oil source is from used vegetable and/or animal oil and/or fat, by-products of the chemical and physical refining of vegetable and/or animal oil and/or fat, by-products of the refining of glycerine from biodiesel, fatty acids from distillation and non-distillation, trap grease, hydrolytically cleaved fatty substances, distilled and non-distilled fatty acids resulting from the cleaving of soap, or mixtures thereof.

4. The method of claim 3, wherein oil source is from used vegetable oil or by-products of the chemical and physical refining of vegetable oil.

5. The method of claim 1, wherein the oil source has an acid number of at least 40 mg KOH/g oil source.

6. The method of claim 1, wherein the at least one free fatty acid is a fatty acid or a mixture of fatty acids selected from caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linolelaidic acid, alpha-linoleic acid, arachidonic acid, eicosapentaenoic acid, erucic acid and/or docosahexaenoic acid.

7. The method of claim 1, wherein in step a) the temperature does not exceed 170° C.

8. The method of claim 1, wherein in step a) the temperature is at least 120° C.

9. The method of claim 1, wherein the catalyst comprises at least methanesulfonic acid.

10. The method of claim 1, wherein the reaction in step a) has a reaction time of more than one hour and less than 12 hours.

11. The method of claim 1, wherein the reaction in step a) is carried out under reduced pressure.

12. The method of claim 1, wherein in step a) the initial molar ratio of glycerol to free fatty acid calculated on the basis of the acid number of the oil is from 1:2 to 1:1.

13. The method of claim 1, wherein in step a) the amount of the methanesulfonic acid or the homoanhydride thereof is from 0.2 to 0.6 weight-% based on the total amount of the oil.

14. The method of claim 1, wherein in step c) the isolation further comprises a distillation step.

15. The method of claim 1, wherein between step a) and step b) no phase separation is carried out.

16. The method of claim 1, wherein after step a) and before step b) the methanesulfonic acid or the homoanhydride thereof and optionally residual free fatty acid is neutralized.

17. The method of claim 1, wherein step a) is carried out in the presence of at least one anionic surfactant S.

18. The method of claim 4, wherein oil source is coconut oil, corn oil, cottonseed oil, olive oil, palm oil, peanut oil, rapeseed oil, safflower oil, sesame oil, soybean oil, sunflower oil, palm fatty acid distillate or palm sludge oil.

19. The method of claim 4, wherein the oil source has an acid number of at least 60 mg KOH/g oil source.

20. The method of claim 1, wherein the at least one free fatty acid comprises oleic oil and/or palmitic acid.

\* \* \* \* \*